United States Patent [19]

Sage, Jr.

[11] Patent Number: 5,284,471
[45] Date of Patent: Feb. 8, 1994

[54] ELECTRODE AND METHOD USED FOR IONTOPHORESIS

[75] Inventor: Burton H. Sage, Jr., Raleigh, N.C.

[73] Assignee: Becton, Dickinson and Company, Franklin Lakes, N.J.

[21] Appl. No.: 545,214

[22] Filed: Jun. 28, 1990

Related U.S. Application Data

[62] Division of Ser. No. 412,056, Sep. 25, 1989, Pat. No. 4,950,229.

[51] Int. Cl.⁵ .............................................. A61N 1/30
[52] U.S. Cl. ...................................... 604/20; 602/152; 602/148
[58] Field of Search .................. 604/20; 128/798, 799, 128/803

[56]    References Cited
U.S. PATENT DOCUMENTS

| | | | |
|---|---|---|---|
| 2,047,308 | 7/1936 | Chapman | 128/798 |
| 3,848,608 | 11/1974 | Leonard | 128/799 |
| 4,325,367 | 4/1982 | Tapper | 604/20 |
| 4,398,545 | 8/1983 | Wilson | 128/803 |
| 4,416,274 | 11/1983 | Jacobson et al. | 604/20 |
| 4,543,958 | 10/1985 | Cartmell | 128/803 |
| 4,788,208 | 1/1989 | Faase, Jr. | 128/798 |
| 4,820,263 | 4/1989 | Spevak et al. | 604/20 |
| 4,865,582 | 9/1989 | Sibalis | 604/20 |
| 4,883,457 | 11/1989 | Sibalis | 604/20 |
| 4,950,229 | 8/1990 | Sage, Jr. | 604/20 |
| 5,002,527 | 3/1991 | Reller et al. | 604/20 |
| 5,047,007 | 9/1991 | McNichols et al. | 604/20 |
| 5,088,977 | 2/1992 | Sibalis | 604/20 |

Primary Examiner—Ruth S. Smith
Assistant Examiner—Krista M. Pfaffle

[57]    ABSTRACT

An iontophoretic electrode has a plurality of ion transmitters for establishing electric field lines in an area and a plurality of receivers for accepting ions flowing along the field lines. A plurality of shields are located to resist ion flow between adjacent transmitters and receivers. The transmitters, shields and receivers are in at least a sequence of transmitter, shield, receiver, shield. The electric field lines emanate substantially in one direction and return in substantially the opposite direction. The transmitters and receivers have matrix structures with space to contain ionic medication and electrolyte, respectively. A support for holding a plurality of sequences has current carrying contacts exposed to connect the transmitters and receivers in circuit with a source of electrical power. The preferred method includes establishing an electric field with lines of energy between a plurality of first and second conductors of ions and then passing ions along the energy lines between the conductors. Thereafter the method includes restricting the flow of ions to paths between adjacent first and second conductors and then positioning the first conductors relative to the second conductors so that the energy lines emanate from the first substantially in one direction return to adjacent second conductors in the opposite direction.

16 Claims, 4 Drawing Sheets

ELECTRODE AND METHOD USED FOR IONTOPHORESIS

This is a division of application Ser. No. 412,056, filed Sep. 25, 1989, now U.S. Pat. No. 4,950,220.

BACKGROUND OF THE INVENTION

Field of the Invention

This invention relates to an apparatus for an electrode and method used for iontophoresis, and more specifically, to an electrode and method for use of the electrode for iontophoretic transport of an ionic substance transdermally.

Background

Electrodes have been proposed for use in the transdermal delivery of ionic substances. Electromotive force used with an electrode offers the advantage of controlling the rate of delivery. Skin irritation problems occur such as burns at the surface of the skin due to acids or bases formed by electrolysis of the water based medication or electrolyte. Efforts to minimize irritation have been directed to regulating the level of current, improving the electrical connection of the electrode with the skin and reducing the hydrolysis of the water used in the ionic medication and the electrolyte.

Electrode structures for transdermal drug delivery have an active electrode which delivers the ionic medication and an indifferent electrode with an electrolyte. The active and indifferent electrodes are connected to the skin forming a circuit. The current passes from a power source through one of the electrodes to the skin, through the the skin into the subdermal tissue, back out through the skin at a separate location and then through the other electrode. Regulation of the rat of drug delivery has been controlled by the amount of current flow and that has been limited by the electrical resistance or impedance of skin. Skin irritation is directly related to the aggressiveness of the ionic substances at the interface between the electrode and the skin and the electrical power needed to deliver the medication. The desired delivery rate often cannot be tolerated. Various power sources and electrode arrangements and constructions have been suggested to avoid burns and irritation where the iontophoresis takes place.

The efforts to use voltage levels below that required for hydrolysis as in U.S. Pat. No. 4,752,285 or the use of alternating current to eliminate galvanic action are not entirely effective. The ability to deliver the preferred level of medication without skin irritation is a function of many factors which influence the efficiency with which any medication can be iontopheretically delivered at a preferred rate. In the past the configuration of the electrode has not been considered a factor although various electrode configurations have been proposed.

In U.S. Pat. No. 617,543 a hollow roller electrode of any suitable cross section with wooden insulating strips between metallic conducting strips that are alternately connected to opposite sides of a source of electricity. No specific recognition of iontophoresis or disclosure of contact by more than one set of metallic strips with the skin to complete at one time more than one circuit through the skin are disclosed. Exit valves dispense medication, surround the surface of the hollow electrode which contains the medication and open when in contact with the skin.

Batteries are frequently used as a power source because of their portability and since low voltage direct current is effective. In U.S. Pat. Nos. 222,276 and 770,014 electrode battery combinations are explained. Battery current drives medication or a conducting salt into the body. Zinc and copper electrodes form the battery and in the '276 patent the electrodes are concentric to one another; in the '014 patent the electrodes are of similar construction with surfaces which project through separating insulation. The projections may carry absorbent liquid containing pads placed between the projections and the body.

Supports for the electrodes and the power source have also included reservoirs for the ionic medication. The particular configuration of the support is a function of how much of the iontophoretic apparatus is carried in one package.

U.S. Pat. Nos. 4,164,226 and 4,211,222 disclose a plurality of alternate electrode elements which are claimed to avoid iontophoretic burn by permitting current to be applied over a period of time. The '226 patent has small positive and negative electrodes which are spacially intermingled. The size of the positive electrodes may be the same as the negative or may be larger. A thick porous and preferably moist material is used between the negative electrode and the skin to eliminate iontophoretic burn by preventing the migration of particles from the metallic electrode as the current passes into the skin.

Electrode structures wherein the active and the indifferent electrodes are carried on an insulator separate from each other but in position to contact the skin have taken many forms. U.S. Pat. No. 4,325,367 has an electrode support structure on which is mounted a pair of electrodes in proximity to one another and a source of electrical power for the electrodes. U.S. Pat. No. 4,406,658 shows an iontophoresis device with an active electrode from which the ionic substance is driven into the body and an indifferent or ground electrode used to complete the electrical circuit through the body. The ionic substance can be positively or negatively charged but the active electrode must also be positively or negatively charged, respectively. The electrodes in U.S. Pat. No. 4,406,658 are adhesive so as to adhere to the skin. The electrodes are held on a support and spaced apart by a projection between them. A battery is also carried in the support and a switch for reversing the polarity of the power supply to the electrodes.

U.S. Pat. No. 4,622,031 has multilayer electrode with a peripheral contact lip as one electrode element surrounding the other electrode element. Current from a battery in that multilayer package drives the ions from the reservoir into the skin; a LED indicates current flow through the lip and into the skin by means of electrical connection to the skin with a conductive adhesive. U.S. Pat. No. 4,640,689 discloses a pair of side by side active and indifferent electrodes. At least two electrode elements are within a cover partially enclosing a reservoir which is in one of the elements. A semi permeable member in one element forms a drug gradient when power is applied from the source through a conductive adhesive to the skin.

Many materials have been suggested and used as conductive electrodes including metallic and porous natural and polymer structures depending upon what drug is desired to be delivered. U.S. Pat. No. 4,708,716 discloses a plurality of cells or reservoir units with flexible separations therebetween to provide flexibility of the electrode to conform to the contours of the body. Each cell or unit is surrounded by a nonconductive gel. U.S. Pat. No. 4,713,050 has a layered electrode construction with a reservoir having a cover, lip and adhesive. U.S. Pat. No. 4,731,926 discloses a method of manufacture of a multi reservoir device which is layered and lipped in configuration. The method of making the reservoirs includes occluding foam to provide insulators between the reservoirs/elements.

U.S. Pat. No. 4,734,090 discloses techniques recognizing the principle that the sweat ducts have less resistance to the flow of current and therefore ions so as to direct the current to the stratum corneum or to circumvent the stratum corneum or by using a system which plugs the entrances to the ducts. U.S. Pat. No. 4,653,501 shows a electrode construction wherein the metal conductor can be reused and the electrode pad can be replaced such that the more expensive part of the electrode is retained and the body contact part of the electrode is disposable. U.S. Pat. No. 4,416,274 shows an electrode for iontophoresis which has structure to inhibit the migration of ions laterally or in a direction parallel to the surface of the skin in order to decrease the likelihood of burns.

West German Patent DE 3,020,789 discloses a electrode which may be used to deliver medication applied to the body and underneath the electrode such that direct current through the electrode will drive the medication into the body. An adjustable electrode with a slidable support coupling holds adjustably positioned arms for placement of the electrodes in spaced apart relation. Thus current can be applied to different parts of the body and the spacing between the electrodes can be adjusted. International patent application WO88/00846 discloses an electrode which can be carried on a wrist belt.

Missing from these patents is the fundamental concept of having multiple active and indifferent elements separated by an insulator wherein the spacing of the elements provides electric field lines located for transdermally delivering drug to a required depth. The unappreciated advantages of such multiple elements are improved power efficiency and the discovery that the amount of separation of the elements relates to the penetration depth of the iontophoretic delivery of medication. Improved power efficiency and the relationship of electrode spacing to depth of drug delivery result from placement of the active and indifferent elements against an insulator which sets the spacing and accordingly the depth of iontophoretic transdermal penetration.

SUMMARY OF THE INVENTION

An iontophoretic electrode array for use in transdermal transport of ionic solutions through mammalian skin has a plurality of ion transmitters for establishing electric field lines in an area and for transmission of ions along the lines. Each transmitter has a pair of longer sides and a pair of shorter sides. A plurality of receivers are positioned for accepting ions flowing along the electric field lines. Each receiver has a pair of longer sides and a pair of shorter sides. A plurality of shields of a substance to resist the flow of ions thereacross are located between adjacent transmitters and receivers along the longer sides thereof. The preferred array has the shields interposed between adjacent transmitters and receivers so that the transmitters, shields and receivers are arranged in at least a sequence of transmitter, shield, receiver, shield.

The aspect ratio of the longer to the shorter sides of the respective transmitters and receivers is in the preferred embodiments greater than one and one half. The aspect ratio of the longer to the shorter sides of the respective transmitters and receivers is most preferably in the range of four to twenty. The electric field lines emanate substantially in one direction transversely across the longer sides of the transmitters and the receivers and the electric field lines return through the area to adjacent receivers in directions substantially opposite the one direction. The transmitters may have a matrix structure with space therein to contain ionic medication and the matrix structure is preferably a porous substance. Similarly, the receivers can have a matrix structure with space therein to contain electrolyte and also be a porous substance.

A support for holding a plurality of sequences of transmitters and receivers separated by interposed shields may be included on the array. The support has current carrying contacts positioned thereon and exposed to connect the transmitters and receivers in circuit with a source of electrical power. In addition, the source of electrical power is preferably carried in the support.

In one form of the array the transmitters and receivers are rectangular plate like in shape with a pair of opposed parallel major surfaces bound by sides set perpendicular thereto and a first set of current carrying contacts are connected in circuit with the source of electrical power and are exposed to connect with one of the sides of each of the transmitters. Similarly, the support has a second set of current carrying contacts positioned thereon and exposed to connect one of the sides of each of the receivers in circuit with the source of electrical power. The first and second sets of the contacts are mounted on the support in spaced apart relation relative to each other and are located on a face thereof. The first set of contacts connected to the transmitters are arranged in circuit for passing electrons between the source of electrical power to the transmitters, and the second set of contacts connected to the receivers are arranged in circuit for passing electrons between the receivers and the power sources so that there is current flow from the source of electrical power to the transmitters and there is current flow from the receivers to the source of electrical power when ions flow between the sides of the transmitters opposite the first set of contacts and the adjacent sides of the receivers opposite the second set of contacts through the skin. The support may include recesses so that each shield may extend beyond the face thereon into one recess.

The array may be used to deliver ionic medication by iontophoresis in a preferred method including establishing an electric field having lines of energy between a plurality of first conductors of ions and a plurality of second conductors of ions. The method has the next step of passing ions along the energy lines of the electric field from the first to the second conductors and through a resistive medium. Thereafter the method includes restricting the flow of ions to paths between adjacent first and second conductors defined by the energy lines of the electric field. The method has the step of positioning the first conductors relative to the second conductors so that the energy lines emanate therefrom substantially in one direction return to the adjacent second conductors in another direction opposite the one direction.

DETAIL DESCRIPTION

Figure 1:
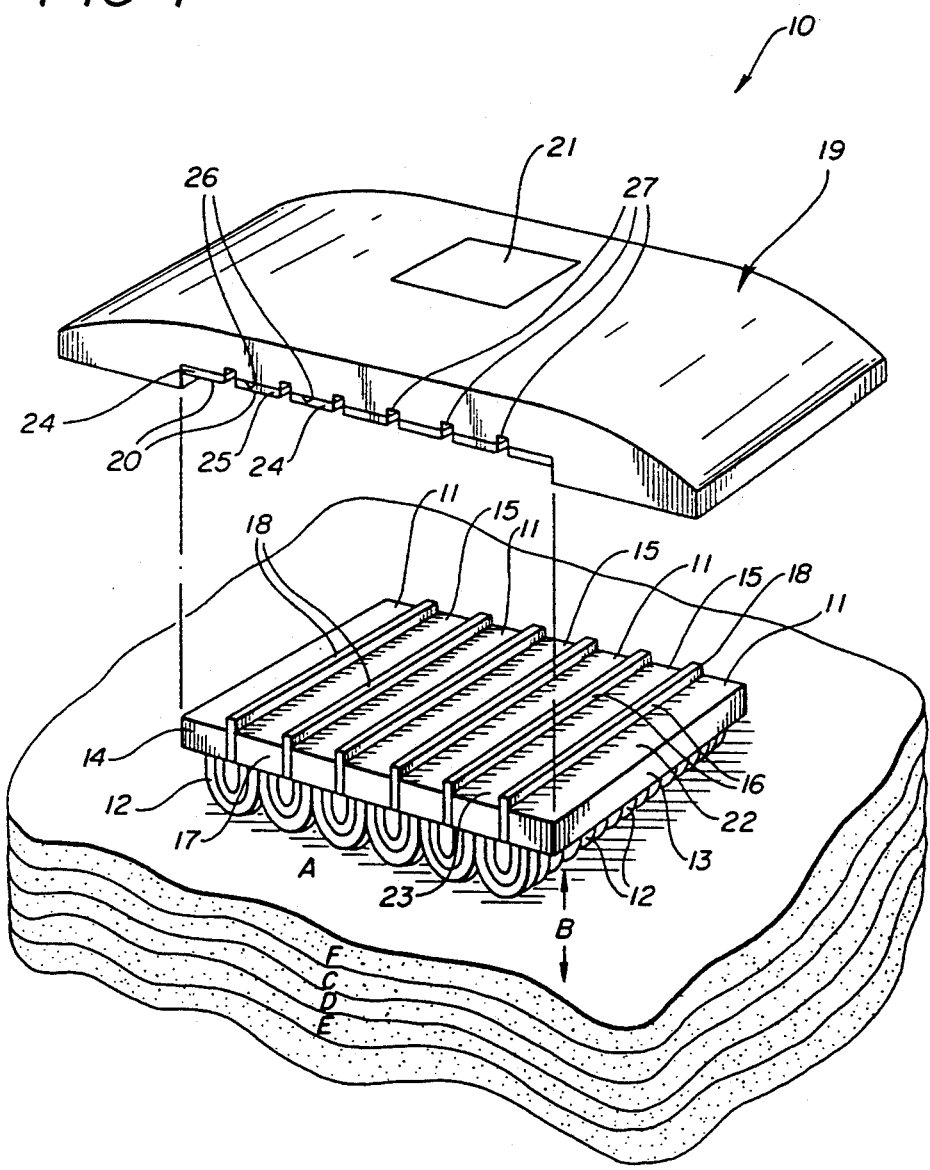
FIG. 1 is an exploded perspective view of the preferred embodiment of an ionotophoretic electrode array.

While this invention is satisfied by embodiments in many different forms, there is shown in the drawings and will herein be described in detail a preferred embodiment and alternate embodiments of the invention, with the understanding that the present disclosure is to be considered as exemplary of the principles of the invention and is not intended to limit the invention to the embodiments illustrated. The scope of the invention will be measured by the appended claims and their equivalents.

An iontophoretic electrode array 10 for placement against the skin during transdermal transport of ionic solutions through mammalian skin is shown in perspective in FIG. 1. The array 10 has a plurality of ion transmitters 11 for establishing electric field lines 12 in an area A for placement against the skin and for transmission of ions along the field lines 12. Each transmitter 11 is configured to have a pair of longer sides 13 and a pair of shorter sides 14. The array 10 also includes a plurality of receivers 15 in position for accepting ions flowing along the electric field lines 12 in the area A of the skin. The shape of each receiver 15 has a pair of longer sides 16 and a pair of shorter sides 17.

A plurality of shields 18, made of a substance to resist the flow of ions thereacross, are in the array 10. The shields 18 are interposed and located between adjacent transmitters 11 and receivers 15 in between the longer sides 13 and 16 thereof so that the transmitters 11, shields 18 and receivers 15 are arranged in at least a sequence of transmitter 11, shield 18, receiver 15, shield 18. The electric field lines 12 are generally transverse to the longer sides 13 and 16 as they pass through the area A of the skin.

The aspect ratio of the longer sides 13 and 16 to the shorter sides 14 and 17 of the respective transmitters 11 and receivers 15 is greater than one and one half to one. The preferred range for the aspect ratio between four and twenty for the longer sides 13 and 16 to the respective shorter sides 14 and 17. The transmitters 11 are made of a material which contains ionic medication. The material is a porous substance with space therein to contain ionic medication. The material in one form of the invention is a hydrogel formulated to include the ionic medication.

The receivers 15 include a material which contains an electrolyte. The material is a porous substance with space therein to contain the electrolyte. The material in one form of the unit is surrounded by a nonconductive gel. U.S. invention is a hydrogel so formulated to include the electrolyte. The transmitters 11 could alternatively be a matrix structure with space therein to contain ionic medication and likewise the receivers 15 could have a matrix structure with space therein to contain electrolyte. The matrix structure is a porous substance such as Porex brand polymer.

The electrode array has a support 19 for holding a plurality of sequences of transmitters 11 and receivers 15 separated by interposed shields 18. The support 19 has current carrying contacts 20 positioned thereon and exposed to connect the transmitters 11 and receivers 15 in circuit with a source of electrical power 21. The source of electrical power 21 is carried in the support 19. The transmitters 11 and receivers 15 are rectangular plate like in shape with the pair of longer sides 13 and 16 being opposed parallel major surfaces 22 and 23 bound by the shorter sides 14 and 17 perpendicular thereto. In one form of the array 10 the support 19 has a first set of current carrying contacts 24 connected in circuit with the source of electrical power 21 and positioned thereon and exposed to connect to the top of each of the transmitters 11 and wherein the support 19 has a second set of current carrying contacts 25 positioned thereon and exposed to connect the top of each of the receivers 15 in circuit with the source of electrical power 21.

The first and second sets of the contacts 24 and 25 are mounted on the support 19 in spaced apart relation relative to each other and are located on a face 26 thereof, the first set of contacts 24 connected to the transmitters 11 are arranged in circuit for passing current from the source of electrical power 21 to the transmitters 11 and the second set of contacts 25 connected to the receivers 15 are arranged in circuit for receiving ions from the receivers 15 so that there is current flow from the source of electrical power 21 to the transmitters 11 and there is current flow from the receivers 15 to the source of electrical power 21 when ions flow between the sides of the transmitters 11 opposite the first set of contacts 24 and the adjacent sides of the receivers 15 opposite the second set of contacts 25.

The support 19 includes recesses 27 and each shield 18 when assembled extends beyond the face 26 thereon for the first and second contact sets 24 and 25 into one recess 27 in the support 19 so that each recess 27 locates the transmitters 11 and the first set of contacts 24 in circuit and aligns the receivers 15 and the second set of contacts 25 in circuit.

Figure 2:
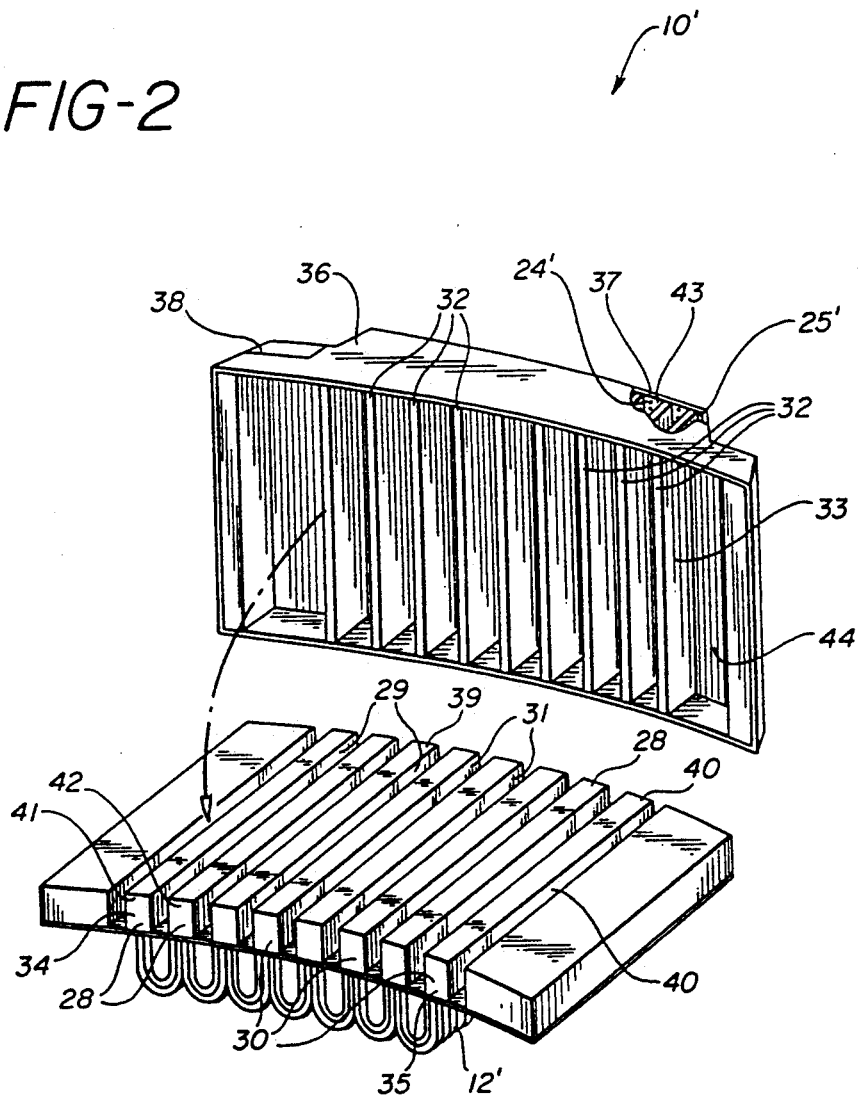
FIG. 2 is an exploded perspective view of an alternate iontophoretic electrode array.

In FIG. 2 an alternate embodiment of an array 10' has a plurality of active members 28, each active member 28 generally rectangular in shape and having a pair of longer sides 29 opposite each other. Each active member 28 is made of a material for containing an ionic medication solution. A plurality of indifferent members 30 is in the array 10' and each indifferent member 30 is of generally rectangular shape having a pair of longer sides 31 opposite each other. Each indifferent member 30 is made of a material for containing an electrolyte solution. A plurality of insulators 32 is included in the array 10' so each insulator 32 has a pair of sides 33 opposite each other and each insulator 32 is when assembled placed in side 33 against side 33 contact with and between the active and indifferent members 28 and 30 forming the array 10' having at least the sequence of active member 28, insulator 32, indifferent member 30, insulator 32.

The placement of the insulators 32 is such that the longer sides 29 and 31 of the generally rectangular active and indifferent members 28 and 30 are against the insulators 32 in the sequence. Because of the generally rectangular shape the aspect ratio of the longer to the shorter sides 34 and 35 of the respective active and indifferent members 28 and 30 is greater than one and one half to one. The aspect ratio of the longer sides 29 and 31 to the shorter sides 34 and 35 of the respective active and indifferent members 28 and 30 is preferably in the range of four to twenty.

The array 10' includes a support 36 for holding a plurality of active members 28 and indifferent members 30 separated by interposed insulators 32. The support 36 carries contacts 37 positioned thereon and exposed to connect the active and indifferent members 28 and 30 in circuit with a source of electric power 38. The source of electric power 38 is carried by the support 36. The longer sides 29 and 31 of the active and indifferent members 28 and 30 are major surfaces 39 and 40 respectively, with each of the members 28 or 30 having a pair of opposed marginal planes 41 for the active member 28 and 42 for the indifferent member, wherein the planes 41 and 42 are located normal to the major surfaces 39 and 40, respectively.

The support 36 has contacts 37 shown in the cut away portion of the support 36 of FIG. 2, includes a first set of current carrying contacts 24' connected in circuit with the source of electrical power 38 and positioned on the support 36 and exposed to connect with one of the marginal planes 41 of each of the active members 28. The support 36 has a second set of current carrying contacts 25' in circuit with the source of electrical power 38 and positioned thereon and exposed to connect with one of the marginal planes 42 of each of the indifferent members 30. The first and second sets of the contacts 24' and 25' are mounted on the support 36 in spaced apart relation relative to each other and are located on a face 43 thereof; the first set of contacts 24' connected to the active members 28 are arranged in circuit for passing current from the source of electrical power 38 to the active members 28 and the second set of contacts 25' connected to the indifferent members 30 arranged in circuit for passing current to the source of electrical power 38 so that there is current flow from the source of electrical power to the active members 28 and there is current flow from the indifferent members 30 to the source of electrical power 38 when there are ions flowing along electrical field lines 12' between active members 28 opposite the first set of contacts 24' and indifferent members 30 opposite the second set of contacts 25'.

In this form of the array 10' the insulator 32 between each of the active and indifferent members 28 and 30 respectively, extends beyond the face 43 thereof for locating the first and second sets of contacts 24' and 25' and the support 36 has a plurality of grooves 44 positioned to locate the active members 28 and the first set of contacts 24' in circuit and to align the indifferent members 30 and the second set of contacts 25' in circuit when the active and indifferent members 28 and 30, insulators 32 and the support 36 are assembled with the major surfaces 39 and 40 thereof against the insulators 32 therebetween.

The active members 28 have a matrix structure with space therein to contain ionic medication and the indifferent members 32 have a matrix structure with space therein to contain electrolyte. The matrix is a porous polymer of polyethylene.

Figure 3:
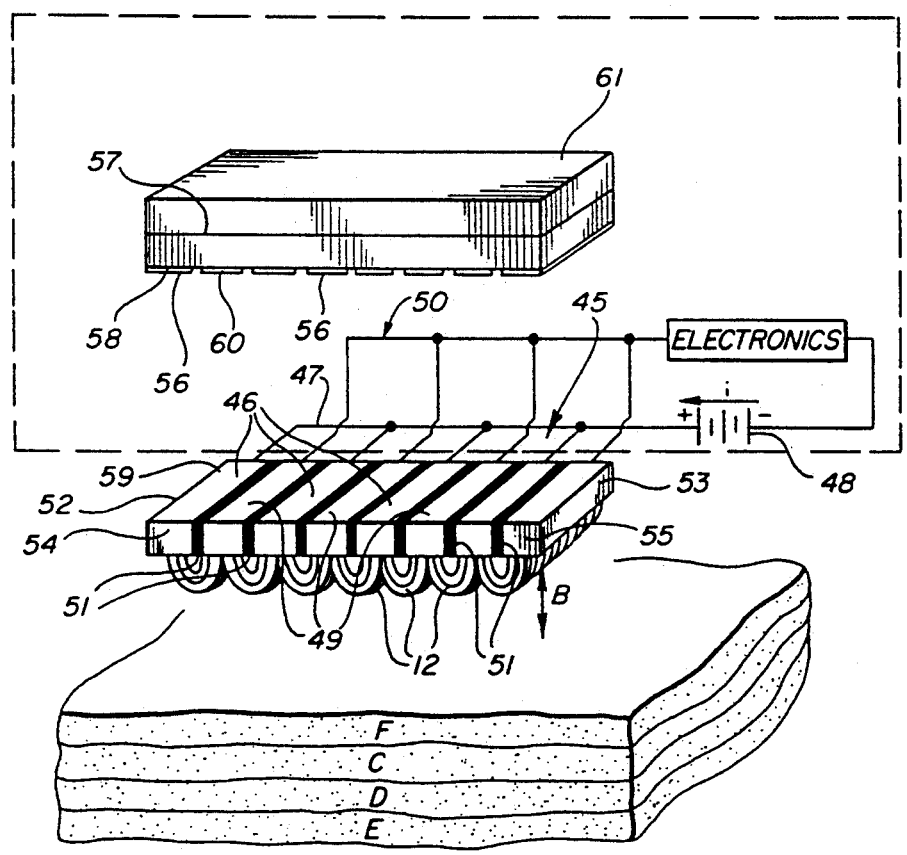
FIG. 3 is an exploded schematic of an alternate iontophoretic electrode illustrated in perspective.

An alternate iontophoresis electrode 45 shown schematically in FIG. 3, has a plurality of first conductors 46 electrically connected in parallel to a first output 47 of a source of electrical power 48. Each of the first conductors 46 has an elongate configuration bound on opposite sides and made of a material to readily pass ions thereacross. A plurality of second conductors 49 in the electrode 45 is electrically connected in parallel to second output 50 of the source of electrical power 48. Each of the second conductors 49 has an elongate configuration bound on opposite sides and made of a material to readily pass ions thereacross. A plurality of insulators 51 of electrically non conductive material are in the electrode 45. Each of the insulators 51 has an elongate configuration bound on opposite sides and is made of a material which resists the passage of ions thereacross.

The placement of the insulator 51 material which resists the flow of ions is such that longer sides 52 and 53 of the elongate first and second conductors 46 and 49 are against the insulator 51 material which resists the flow of ions. Because of the generally elongate shape the aspect ratio of the longer sides 52 and 53 to the shorter sides 54 and 55 of the respective first and second electrical conductors 46 and 49 is greater than one and one half to one. The aspect ratio of the longer to the shorter sides of the respective first and second conductors 46 and 49 is preferably in the range of four to twenty. The insulator 51 material which resists the flow of ions is interposed between first and second conductors 46 and 49 for forming a sandwich construction.

A support 56 is attached to the electrode 45 with a plurality of first contacts 57 are positioned in spaced apart relation thereon on a face 58 thereof. The first contacts 57 are electrically connected in a first parallel circuit with the source of electrical power 48 such as a battery and one side 59 of each of the first conductors 46. The support 56 has a plurality of second contacts 60 positioned thereon on the face 58 thereof and in spaced apart relation. The second contacts 60 are electrically connected in a second parallel circuit with the source of electrical power 59 and one side of each of the second conductors 49.

Although schematically shown within a dashed line, the support 56 carries above the face 58 the source of electrical power 48. The support 56 includes a reservoir 61 in fluid connection with the first conductors 46 and adapted to contain ionic material for transdermal transport by the first conductors 46. The reservoir 61 is detachably contained on the support 56 so that the reservoir 61 can be removed and replaced.

A method of using an iontophoresis electrode 45 for transdermal transport of an ionic substance is also a part of this invention. The method includes the steps of establishing electric field lines 12 of energy between the plurality of first conductors 46 of ions and the plurality of second conductors 49 of ions. Then the method includes the step of passing ions along the energy lines 12 of the electric field from between the plurality of first to the second conductors 46 and 49 and through a semiconductive medium. Thereafter the step includes restricting the flow of ions to paths between adjacent first and second conductors 46 and 49 defined by the energy lines 12 of the electric field. The next step is positioning the first conductors 46 relative to the second conductors 49 so that the energy lines 12 emanate therefrom substantially in one direction return to the adjacent second conductors 49 in another direction opposite the one direction shown as perpendicular to the skin by arrow B, in FIGS. 1 and 3.

The thickness of the shields 18 or insulators 32 or 51 has a an effect upon how deeply the ionic solution is transported into the skin. For a range of thickness between very thick and very thin shields 18 or insulators 32 or 51, the electric field lines 12 are still relatively short, and hence require relatively low energy to transport the ionic solution. The electric field lines 12 are sufficiently long, however, so that the ionic solution is still transported by the electric field lines 12 to the epidermis at C and dermis at D for transfer to the vasculature at E. To some extent, the preferred range extends from 0.01 to 1.0 inches or 0.025 to 2.5 centimeters. The most beneficial range is 0.10 to 0.62 centimeters.

The stratum corneum at F is essentially unhydrated protein. Since there are few ions in that material the impedence is high. The granulated epidermis C is the sight of transformation from the well hydrated basal epidermis C to the unhydrated stratum corneum F. Here the impedence falls off as the tissue increases in hydration, also because of salt content. From the basal epidermis C inward, tissues are well hydrated, and salt solutions isotonic whereby the impedence nears its minimum. Of course, the impedence will vary from person to person and place to place on any liven person, however, it is known that the impedence is high at the stratum corneum F gradually decreasing to the granulated epidermis where it drops significantly and remains low into and through the basal epidermis C and the dermis D. For very thin shields 18 or insulators 32 or 51 in a repeated array 10 or 10' or in an electrode 45 such as disclosed and described as the embodiments in this specification, the electric field lines 12 pass through the stratum corneum F and maybe the upper layers of the granulated epidermis C.

These paths are preferred in spite of the high resisitivity or impedence of the stratum corneum F because the path lengths of the electric field lines 12 are short. Since ionic solution flows during transportation along the electric field lines 12, it can be appreciated that the ionic solution is transported well into the stratum corneum F then flows backup to the receiver. Thus, for very thin insulators, little of the medication reaches the blood stream. Moreover, this approach has the greatest likelihood to actually short out due to the close spacing of either the transmitters and receivers 11 and 15, the active and indifferent members 28 and 30 or the first and second conductors 46 and 49.

If the shields 18 or insulators 32 or 51 are very thick, the electric field lines 12 lengthen as they take the path of least impedence through the stratum corneum F and the hydrated tissue C below the stratum corneum F so they may return through the stratum corneum F to the next adjacent transmitter 11 or receiver 15, member 28 or 30, or conductor 46 or 49, requiring greater levels of energy. This path is most effective for transportation of ionic solution to the dermis D, however, it requires the greatest amount of energy which increases the amount of skin damage or irritation. An optimum thickness of insulator 32 or 51 or shield 18 exists wherein the field lines are deep enough to cause ions to reach the bloodstream, and the length of each field line is short enough to minimize skin irritation.

Figure 4:
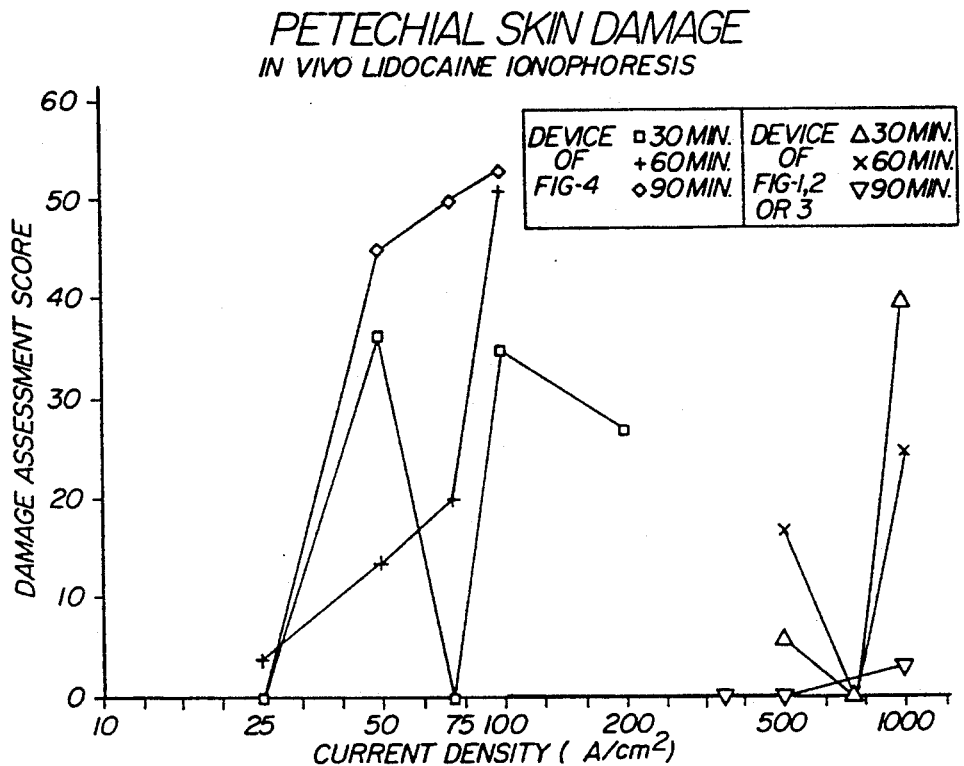
FIG. 4 is a graph of current density relative to skin damage for experiments with a pair of spaced electrodes and with arrays of the type disclosed in FIGS. 1, 2 or 3.
Figure 5:
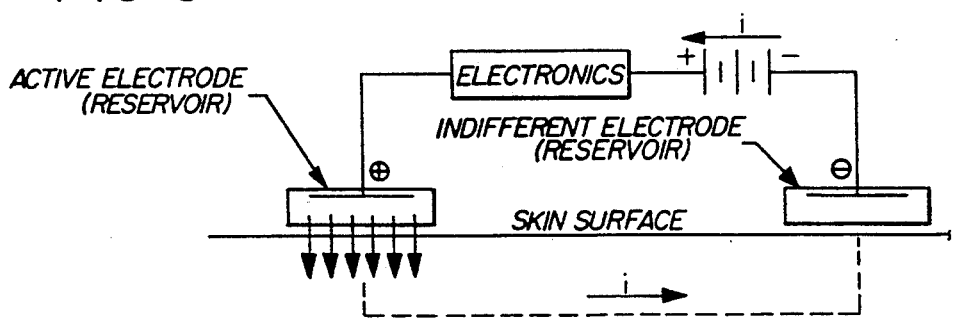
FIG. 5 is a schematic side elevational view of the pair of spaced electrodes used to obtain some of the data in the graph of FIG. 4.

FIG. 4 is a plot on a graph of the petechial skin damage of an experiment with iontophoretically transported lidocaine. Along the vertical axis of that graph is shown the damage assessment score which is the number of petechial (small, punctate, red spots in the skin) observed under the electrode. This axis is linearly divided, the horizontal axis shows current density necessary in order to transport ionic solution. The current density is in microamps per square centimeter and the scale is a log scale. The significant data are represented by two areas of the plot. The first area of the graph is plotted above the current density range of 25 to 75 microamperes per square centimeter for a typical iontophoretic electrode of the type in FIG. 5 wherein the active and indifferent members are spaced apart and are of no particular shape as can be seen, damage to the skin begins to occur at current densities of about 25 microamperes.

The second plot of data in the range of 500 to 1000 microamperes per square centimeter represent the experiments with the claimed invention. The difference in these data are apparent in that the amount of current density that can be used without damage to the skin is at least ten times greater than with the schematic showing of an electrode having active and indifferent electrodes with a circuit therebetween in FIG. 5. Another way of looking at the data is that current between 100 and 500 microamperes per square centimeter can be used to transport drug without measurable damage using this invention. Note that several data points are not typical of that which is expected; those data points show the difficulty of transportation caused by variations of impedence of the skin. These particular data were obtained during experiments with pigs where the damage was assessed after each test upon a different area of the animal's skin.

The specific material described and the particular configurations of the preferred and alternate embodiments may be changed without departing from the scope of the invention covered by the claims which follow.

What is claimed is:

1. An electrode array comprising:
   a plurality of rectangular active members, each active member having a pair of long sides opposite each other and opposed end surfaces, each of said active members made of a material for containing an ionic medication solution;
   a plurality of rectangular indifferent members each having a pair of long sides opposite each other and opposed end surfaces, each of said indifferent members made of a material for containing an electrolyte solution; and
   a plurality of insulators each having a pair of sides opposite each other, each of said insulators placed in side against side contact with and between the long sides of said active and indifferent members which are spaced and parallel to each other forming an array having at least the sequence of active member, insulator, indifferent member, insulator.

2. The electrode array of claim 1 wherein the rectangular active members and the rectangular indifferent members have a common aspect ratio.

3. The electrode array of claim 2 wherein the aspect ratio is greater than one and one half.

4. The electrode array of claim 1 including support means for holding said plurality of active members and said indifferent members separated by said interposed insulators.

5. The electrode array of claim 4 further including a circuit wherein said support means has current carrying contacts positioned thereon, wherein said contacts connect the active and indifferent members to said circuit includes a source of electric power.

6. The electrode array of claim 5 wherein the source of electric power is a battery and said support means including means for engaging said battery.

7. The electrode array of claim 5 wherein said current carrying contacts include a first set of current carrying contacts connected in circuit with the source of electrical power and positioned on said support means and exposed to connect with one of the end surfaces of each of the active members and a second set of current carrying contacts positioned on said support means and exposed to connect with one of the end surfaces of each of the indifferent members in circuit with the source of electrical power.

8. The electrode array of claim 7 wherein the first and second sets of the contacts are mounted on the support means in spaced apart relation relative to each other and are located on a face thereof, the first set of contacts connected to the active members are arranged in circuit for passing current from the source of electrical power to the active members and the second set of contacts connected to the indifferent members are arranged in circuit for passing current to the source of electrical power so that when said electrode array is placed against mammalian skin there is current flow from the source of electrical power to the active members and there is current flow from the indifferent members to the source of electrical power.

9. The electrode array of claim 8 wherein each of said insulators between each of the active and indifferent members extends beyond the face and the support means has a plurality of grooves positioned to locate the active members and the first set of contacts in circuit and to align the indifferent members and the second set of contacts in circuit.

10. The electrode array of claim 1 wherein the active members have a matrix structure with space therein adapted for receiving ionic medication and the indifferent members have a matrix structure with space therein adapted for receiving electrolyte.

11. The electrode array of claim 10 wherein the matrix structure is a porous polymer.

12. An iontophoresis electrode comprising:
a plurality of first ionic conductors electrically connected in parallel for connection to a first output of a source of electrical power, each of the first conductors having an elongate configuration including a plurality of elongate sides and made of a material to readily pass ions thereacross;
a plurality of second ionic conductors electrically connected in parallel for connection to a second output of the source of electrical power, each of the second conductors having an elongate configuration including a plurality of elongate sides and made of a material to readily pass ions thereacross;
a plurality of insulators of electrically non-conductive material, each of the insulators having an elongate configuration including a plurality of elongate sides and made of a material which resists the passage of ions thereacross, the insulators each interposed between said first and second conductors for forming a sandwich construction; and
a support having a plurality of first contacts positioned thereon on a face thereof and in spaced apart relation, the first contacts electrically connected in a first parallel circuit with one elongate side of each of the first conductors, the support having a plurality of second contacts positioned thereon on the face thereof and in spaced apart relation, the second contacts electrically connected in a second parallel circuit with one elongate side of each of the second conductors, the support including means for engaging a source of electrical power to said first and second parallel circuits.

13. The electrode of claim 12 wherein an aspect ratio of the elongate first conductors is greater than one and one half.

14. The electrode of claim 12 wherein an aspect ratio of the elongate second conductors is greater than one and one half.

15. The electrode of claim 12 wherein the support includes reservoir means for fluid communication with the first conductors and adapted to contain ionic material for transdermal transport by the first conductors.

16. The electrode of claim 15 wherein said support includes means for detachably retaining said reservoir means so that said reservoir means can be removed and replaced.

* * * * *